United States Patent [19]

Jonczyk et al.

[11] Patent Number: 5,705,481
[45] Date of Patent: Jan. 6, 1998

[54] CYCLOPEPTIDES

[75] Inventors: Alfred Jonczyk, Darmstadt; Günter Holzemann, Seeheim, both of Germany; Brunhilde Felding-Habermann, La Jolla, Calif.; Friedrich Rippmann, Heidelberg, Germany; Guido Melzer, Hofheim/Ts, Germany; Beate Diefenbach, Darmstadt, Germany

[73] Assignee: Merck Patent Gesellschaft mit beschrankter Haftung, Darmstadt, Germany

[21] Appl. No.: 436,601

[22] Filed: May 8, 1995

Related U.S. Application Data

[63] Continuation-in-part of Ser. No. 147,519, Nov. 5, 1993, abandoned.

[30] Foreign Application Priority Data

Nov. 6, 1992 [DE] Germany ............... 42 37 456.1

[51] Int. Cl.$^6$ ............... A61K 38/08; A61K 38/12; C07K 7/64
[52] U.S. Cl. ............... 514/11; 514/9; 514/17; 530/317; 530/330
[58] Field of Search ............... 514/11, 9, 17; 530/317, 330

[56] References Cited

U.S. PATENT DOCUMENTS

| | | | |
|---|---|---|---|
| 4,472,305 | 9/1984 | Hansen et al. | 260/112.5 R |
| 4,713,367 | 12/1987 | Sisto et al. | 530/314 |
| 4,816,449 | 3/1989 | Hahn | 514/17 |

FOREIGN PATENT DOCUMENTS 0406428  1/1991  European Pat. Off.

OTHER PUBLICATIONS

Rudinger, j. (Jun. 1976). Peptide Hormones. (ed. J. A. Parsons). University Park Press. Baltimore. pp. 1–7.

Chemical Abstracts, vol. 114, No. 9 (Mar. 4, 1991), p. 481, No. 114:79202w.

Chemical Abstracts, vol. 110, No. 17 (Apr. 24, 1989), p. 312, No. 110:150020k.

Chemical Abstracts, vol. 107, No. 1 (Jul. 6, 1987), p. 476, No. 107:5066p.

Chemical Abstracts, Vo. 103, No. 25 (Dec. 23, 1985), p. 627. No. 103:212136u.

Aumailley et al., "Arg–Gly–Asp constrained within cyclic per strong and selective inhibitors of cell adhesion to vitro fragment P1," *FEBS*, vol. 291, No. 1, pp. 50–54.

Neubert et al., "Synthese cyclischer und cyclisch–verzweigter Tachykinin–Teilsequenzen," *Pharmazie* 40 (1985), H.8, pp. 532–535. Only the abstract was considered. (see p. 532).

Smith et al., "Interaction of Integrins $\alpha_v\beta_3$ and Glycoprotein IIb–IIIa with Fibrinogen," *The Journal of Biological Chemistry*, 1990, pp. 12267–12271.

*Primary Examiner*—Cecilia J. Tsang
*Assistant Examiner*—Anish Gupta
*Attorney, Agent, or Firm*—Millen, White, Zelano, & Branigan, P.C.

[57] ABSTRACT

The invention relates to novel cyclopeptides of the formula I $$\text{cyclo-}(A\text{-}B\text{-}C\text{-}D\text{-}Arg) \qquad I$$

in which

A and B are each independently of one another Ala, Asn, Asp, Arg, Cys, Gln, Glu, Gly, His, Ile, Leu, Lys, Met, Phe, Pro, Ser, Thr, Trp, Tyr or Val;

C is Asp or Asp(O—$C_{1-4}$-alkyl); and

D is Gly or Ala;

at least two of the amino acid radicals stated being present in the D-form;

and their salts.

These compounds act as integrin inhibitors and can be used in particular for the prophylaxis and treatment of disorders of the circulation and in tumor therapy.

23 Claims, No Drawings

CYCLOPEPTIDES

This is a continuation-in-part of application Ser. No. 08/147,519, filed Nov. 5, 1993, now abandoned.

SUMMARY OF THE INVENTION

The invention relates to novel cyclopeptides of the formula I cyclo-(A-B-C-D-Arg)    I in which A and B are each independently of one another Ala, Asn, Asp, Arg, Cys, Gln, Glu, Gly, His, Ile, Leu, Lys, Met, Phe, Pro, Ser, Thr, Trp, Tyr or Val, C is Asp or Asp(O—$C_{1-4}$-alkyl) and D is Gly or Ala, at least two of the amino acid radicals stated being present in the D-form, and their salts.

Similar compounds are known from Pharmazie 40 (8), 532-5 (1985), and FEBS Lett., 291, pp. 50-54 (1991).

An object of the invention is to provide novel compounds having useful properties, in particular those which can be used for the preparation of medicaments.

Upon further study of the specification and appended claims, further objects and advantages of this invention will become apparent to those skilled in the art.

It has been found that the compounds of the formula I and their salts have very useful properties. In particular, they act as integrin inhibitors, in which case they particularly inhibit the interactions of $\beta_3$-integrin receptors with ligands. This action can be demonstrated, for example, by the method which is given by J. W. Smith et al. in J. Biol. Chem. 265, 12267–12271 (1990). It is known that compounds which inhibit or block the $\beta_3$-integrin receptor ligand interactions such as the binding of fibrinogen to $\beta_3$-integrin receptors (adhesion receptor antagonist or ARA) can be used as therapeutic agents for the treatment of osteoporosis, thrombosis, myocardial infarct, arteriosclerosis, inflammations, apoplexy, angina pectoris and tumors. Furthermore, such compounds inhibit cell adhesion in the case of the formation of osteoclasts and are suitable as agents which support angiogenesis and the healing of wounds. In addition, there are anti-inflammatory effects. All these actions can be demonstrated with the aid of methods which are known from the literature.

The compounds can be employed as pharmaceutically active compounds in human and veterinary medicine, in particular for the prophylaxis and the treatment of disorders of the circulation, thrombosis, cardiac infarct, arteriosclerosis, inflammations, apoplexy, angina pectoris, tumors (e.g., melanoma, sarcoma and epithelioma), osteolytic disorders, in particular osteoporosis, angiogenesis and restenosis after angioplasty.

The abbreviations of amino acid radicals shown above and below stand for the radicals of the following amino acids:

Ala alanine
Asn asparagine
Asp aspartic acid
Asp(OR) aspartic acid ($\beta$-ester; R=$C_{1-4}$-alkyl)
Arg arginine
Cys cysteine
Gln glutamine
Glu glutamic acid
Gly glycine
His histidine
Ile isoleucine
Leu leucine
Lys lysine
Met methionine
Phe phenylalanine
Pro proline
Ser serine
Thr threonine
Trp tryptophan
Tyr tyrosine
Val valine.

In addition, the following have the meanings below:

BOC tert.-butoxycarbonyl
CBZ benzyloxycarbonyl
DCCI dicyclohexylcarbodiimide
DMF dimethylformamide
EDCI N-ethyl-N'-(3-dimethylaminopropyl)-carbodiimide hydrochloride
Et ethyl
FMOC 9-fluorenylmethoxycarbonyl
HOBt 1-hydroxybenzotriazole
Me methyl
Mtr 4-methoxy-2,3,6-trimethylphenylsulfonyl
OBut tert.-butyl ester
OMe methyl ester
OEt ethyl ester
POA phenoxyacetyl
TFA trifluoroacetic acid.

If the amino acids mentioned above can occur in several enantiomeric forms, then all these forms and also their mixtures (e.g., the DL-forms) are included above and below, e.g., as constituents of the compounds of the formula I.

The invention further relates to a process for the preparation of a compound of the formula I or one of its salts, characterized in that it is liberated from one of its functional derivatives by treating with a solvolyzing or hydrogenolyzing agent, or in that a peptide of the formula II

H—Z—OH in which

Z is -A-B-C-D-Arg-, -B-C-D-Arg-A-, -C-D-Arg-A-B-, -D-Arg-A-B-C- or -Arg-A-B-C-D-, or a reactive derivative of such a peptide is treated with a cyclizing agent (e.g., dicyclohexylcarbodiimide (DCCI), N-ethyl-N'-(3-dimethylaminopropyl)-carbodiimide (EDCI), benzyltriazolyltetramethyluronium-tetrafluoroborate (TBTU) and diisopropylcarbodiimide (DICI)), and/or in that a basic or acidic compound of the formula I is converted into one of its salts by treating with an acid or base.

The radicals A, B, C, D and Z above and below have the meanings given in the formulae I and II, if not expressly stated otherwise.

In the above formulae, alkyl is preferably methyl, ethyl, isopropyl or tert.-butyl.

The group A is preferably Val, in particular D-Val. B is preferably Phe, in particular D-Phe. C is preferably Asp, in particular D-Asp. D is preferably Gly.

Accordingly, the invention in particular relates to those compounds of the formula I in which at least one of the radicals has one of the preferred meanings given above.

A preferred group of compounds can be expressed by the part formula Ia, which otherwise corresponds to the formula I, but in which A is D-Val,
B is Phe,
C is Asp and
D is Gly or Ala.

The compounds of the formula I and also the starting materials for their preparation are otherwise prepared by known methods, as are described in the literature (e.g., in the standard works such as Houben-Weyl, Methoden der organischen Chemie, (Methods of Organic Chemistry) Georg-Thieme-Verlag, Stuttgart), in particular under reaction conditions which are known and suitable for the reactions. In this context, use can also be made of known variants which are not mentioned in more detail here.

The starting substances can also be formed in situ, if desired, such that they are not isolated from the reaction mixture, but immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which contain appropriate protected amino and/or hydroxyl groups instead of one or more free amino and/or hydroxyl groups, preferably those which carry an amino protecting group instead of an H atom which is bonded to an N atom, e.g., those which correspond to the formula I, but contain an NHR' group (in which R' is an amino protecting group, e.g., BOC or CBZ) instead of an $NH_2$ group.

In addition, starting materials are preferred which carry a hydroxyl protecting group instead of the H atom of a hydroxyl group, e.g., those which correspond to the formula I, but contain an R"O-phenyl group (in which R" is a hydroxyl protecting group) instead of a hydroxyphenyl group.

Several—identical or different—protected amino and/or hydroxyl groups can be present in the molecule of the starting material. If the protective groups present are different from one another, in many cases they can be removed selectively.

The expression "amino protecting group" is generally known and relates to groups which are suitable for protecting (for blocking) an amino group from chemical reactions, but which are easily removable, after the desired chemical reaction has been carried out on other positions of the molecule. Typical groups of this type are, in particular, unsubstituted or substituted acyl, aryl, aralkoxymethyl or aralkyl groups. As the amino protecting groups are removed after the desired reaction (or reaction sequence), their nature and size is otherwise not critical; but those having 1–20, in particular 1–8, C atoms are preferred. The expression "acyl group" is to be taken in its widest sense in connection with the present process. It includes acyl groups derived from aliphatic, araliphatic, aromatic or heterocyclic carboxylic acids or sulfonic acids and in particular alkoxycarbonyl, aryloxycarbonyl and, above all, aralkoxycarbonyl groups. Examples of acyl groups of this type are alkanoyl such as acetyl, propionyl or butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl, FMOC, and arylsulfonyl such as Mtr. Preferred amino protecting groups are BOC and Mtr, and in addition CBZ, FMOC, benzyl and acetyl.

The expression "hydroxy protecting group" is also generally known and relates to groups which are suitable for protecting a hydroxyl group from chemical reactions, but which are easily removable, after the desired chemical reaction has been carried out on other positions of the molecule. Typical groups of which type are the above-mentioned unsubstituted or substituted aryl, aralkyl or acyl groups, and in addition also alkyl groups. The nature and size of the hydroxy protecting groups is not critical, as they are removed again after the desired chemical reaction or reaction sequence; preferred groups are those having 1–20, in particular 1–10, C atoms. Examples of hydroxyl protecting groups are, inter alia, benzyl, p-nitrobenzoyl, p-toluenesulfonyl and acetyl, benzyl and acetyl being particularly preferred. The COOH groups in aspartic acid and glutamic acid are preferably protected in the form of their tert.-butyl esters (e.g., Asp (OBut)).

The functional derivatives of the compounds of the formula I to be used as starting materials can be prepared by customary methods of amino acid and peptide synthesis, such as are described, e.g., in the standard works and patent applications mentioned, and, e.g., also by the Merrifield solid phase method (B. F. Gysin and R. B. Merrifield, J. Am. Chem. Soc., 94, 3102 et seq. (1972)).

The liberation of the compounds of the formula I from their functional derivatives is carried out—depending on the protecting group used—e.g., with strong acids, preferably with TFA or perchloric acid, but also with other strong inorganic acids such as hydrochloric acid or sulfuric acid, or strong organic carboxylic acids such as trichloroacetic acid or sulfonic acids such as benzene or p-toluenesulfonic acid. The presence of an additional inert solvent is possible, but not always necessary. Suitable inert solvents are preferably organic, for example, carboxylic acids such as acetic acid, ethers such as tetrahydrofuran or dioxane, amides such as DMF, halogenated hydrocarbons such as dichloromethane, and in addition also alcohols such as methanol, ethanol or isopropanol and also water.

In addition, mixtures of the above-mentioned solvents are suitable. TFA is preferably used in an excess without addition of a further solvent, perchloric acid in the form of a mixture of acetic acid and 70% perchloric acid in the ratio of preferably 9:1. The reaction temperatures for the cleavage are preferably about 0°–about 50°, especially 15°–30° (room temperature).

The groups BOC, OBut and Mtr can be removed, e.g., preferably using TFA in dichloromethane or with about 3 to 5N HCl in dioxane at preferably about 15°–30°, the FMOC group using preferably an about 5–50% solution of dimethylamine, diethylamine or piperidine in DMF at preferably about 15°–30°.

Protecting groups which can be removed by hydrogenolysis (e.g., CBZ or benzyl) can be removed, e.g., by treating with hydrogen in the presence of a catalyst (e.g., a noble metal catalyst such as palladium, preferably on a carrier such as carbon). Suitable solvents in this case are those mentioned above, in particular, e.g., alcohols such as methanol or ethanol or amides such as DMF. The hydrogenolysis is carried out, as a rule, at temperatures of preferably about 0°–100° and pressures of preferably about 1–200 bar, particularly at 20°–30° and 1–10 bar. Hydrogenolysis of the CBZ group is easily carried out, e.g., on 5–10% Pd-C in methanol or using ammonium formate (instead of $H_2$) on Pd-C in methanol/DMF at preferably about 20°–30°.

Compounds of the formula I can also be obtained by cyclization of compounds of the formula II under the conditions of a peptide synthesis. In this case, the reaction is preferably carried out by customary methods of peptide synthesis, as are described, e.g., in Houben-Weyl, loc. cit., Vol. 15/II, pp. 1–806 (1974).

The reaction is preferably carried out in the presence of a dehydrating agent, e.g., a carbodiimide such as DCCI or EDCI, and in addition propanephosphonic anhydride (compare Angew. Chem. 92, 129 (1980)), diphenylphosphoryl azide or 2-ethoxy-N-ethoxycarbonyl-1,2-dihydroquinoline, in an inert solvent, e.g., a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures of preferably about −10–40, particularly 0°–30° In order to promote intramolecular cyclization before intermolecular peptide bonding, it is preferable to work in dilute solutions (dilution principle).

Instead of compounds of formula II, suitable reactive derivatives of these substances can also be employed in the reaction, e.g., those in which reactive groups are intermediately blocked by protecting groups. The amino acid derivatives of formula II can be used, e.g., in the form of their activated esters which are preferably formed in situ, e.g., by addition of HOBt or N-hydroxysuccinimide.

The starting materials of the formula II are, as a rule, novel. They can be prepared by known methods, e.g., the above-mentioned methods of peptide synthesis and of removal of protective groups.

As a rule, protected pentapeptide esters of the formula R'—Z—OR", e.g., BOC—Z—OMe or BOC—Z—OEt, are initially synthesized, which are first hydrolyzed to give acids of the formula R'—Z—OH, e.g., BOC—Z—OH; the protective group R' is removed from these, by means of which the free peptides of the formula H—Z—OH (II) are obtained.

A base of the formula I can be converted into the appropriate acid addition salt using an acid. Suitable acids for this reaction are in particular those which yield physiologically acceptable salts. Inorganic acids can thus be used, e.g., sulfuric acid, nitric acid, hydrohalic acids such as hydrochloric acid or hydrobromic acid, phosphoric acids such as orthophosphoric acid and sulfamic acid, and in addition organic acids, in particular aliphatic, alicyclic, araliphatic, aromatic or heterocyclic mono- or polybasic carboxylic, sulfonic or sulfuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, and laurylsulfuric acid. Salts with physiologically unacceptable acids, e.g., picrates, can be used for the isolation and/or purification of the compounds of the formula I.

On the other hand, an acid of the formula I can be converted into one of its physiologically acceptable metal or ammonium salts by reaction with a base. Suitable salts here are in particular the sodium, potassium, magnesium, calcium and ammonium salts, and also substituted ammonium salts, e.g., the dimethyl-, diethyl- or diisopropylammonium salts, monoethanol-, diethanol- or triethanolammonium salts, cyclohexyl- or dicyclohexylammonium salts, dibenzylethylenediammonium salts, and furthermore, e.g., salts with N-methyl-D-glucamine or with arginine or lysine.

The novel compounds of the formula I and their physiologically acceptable salts can be used for the production of pharmaceutical preparations by bringing them into a suitable dosage form together with at least one excipient or auxiliary and, if desired, together with one or more other active compound(s). The preparations thus obtained can be employed as pharmaceuticals in human or veterinary medicine. Suitable excipient substances are organic or inorganic substances which are suitable for enteral (e.g., oral or rectal), parenteral (e.g., intravenous injection) or local (e.g., topical, dermal, ophthalmic or nasal) administration or for administration in the form of an inhalant spray and which do not react with the novel compounds, for example, water or aqueous isotonic saline solution, lower alcohols, vegetable oils, benzyl alcohols, polyethylene glycols, glycerol triacetate and other fatty acid glycerides, gelatin, soya lecithin, carbohydrates such as lactose or starch, magnesium stearate, talc cellulose and vaseline. Tablets, coated tablets, capsules, syrups, liquids or drops, in particular, are used for oral administration; film tablets and capsules having gastric juice-resistant coatings or capsule shells are especially of interest. Suppositories are used for rectal administration, and solutions, preferably oily or aqueous solutions, and in addition suspensions, emulsions or implants, are used for parenteral administration. Solutions, e.g., which can be used in the form of eye drops, and in addition, e.g., suspensions, emulsions, creams, ointments or compresses are suitable for topical application. Sprays can be used which contain the active compound either dissolved or suspended in a propellant gas or propellant gas mixture (e.g., $CO_2$ or chlorofluorohydrocarbons) for administration as inhalant sprays. The active compound here is preferably used in micronized form, it being possible for one or more additional physiologically tolerable solvents to be present, e.g., ethanol. Inhalant solutions can be administered with the aid of customary inhalers. The novel compounds can also be lyophilized and the lyophilizates obtained used, e.g., for the production of injection preparation. The injections can be administered as a bolus or as a continuous infusion (e.g., intravenous, intravascular, subcutaneous or intrathecal). The preparations indicated can be sterilized and/or can contain auxiliaries such as preservatives, stabilizers and/or wetting agents, emulsifiers, salts for influencing osmotic pressure, buffer substances, colorants and/or flavorings. If desired, they can also contain one or more other active compounds, e.g., one or more vitamins.

The substances according to the invention can as a rule be administered in analogy to other known commercially available peptides, but in particular in analogy to the compounds described in U.S. Pat. No. 4,472,305, preferably in dosages of about 0.05–500, in particular 0.5–100 mg per dosage unit. The daily dose is preferably about 0.01–2 mg/kg of body weight. The specific dose for each intended patient depends, however, on many different factors, for example, the activity of the specific compound employed, the age, body weight, general state of health, sex, the cost, the time and route of administration, and the rate of excretion, pharmaceutical combination and severity of the particular disorder to which the therapy applies. Parenteral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 42 37 456.1, filed Nov. 6, 1992, are hereby incorporated by reference.

EXAMPLES

All temperatures above and below are stated in °C. In the following examples, "customary working up" means: water is added, if necessary, the mixture is neutralized and extracted with ether or dichloromethane, the organic phase is separated off, dried over sodium sulfate, filtered and evaporated and the residue is purified by chromatography on silica gel and/or crystallization. RT=retention time (minutes for HPLC on a Lichrosorb RP select B (250–4.7 μm) column, eluent: 0.3% TFA in water; isopropanol gradient of 0–80 vol. % in 50 min. at 1 ml/min. Flow and detection at 215 nm. M⁺=molecular peak in the mass spectrum, obtained by the fast atom bombardment method.

Example 1

A solution of 30 mg of cyclo-(D-Val-L-Phe-D-Asp(OBut) -Gly -D-Arg(Mtr)) [obtainable by cyclization of H-D-Arg (Mtr)-D -Val-L-Phe-D-Asp(OBut)-Gly-OH according to the method given in Example 2] in 840 μl of TFA, 170 μl of dichloromethane and 85 μl of thiophenol is allowed to stand at 20° for 2 hours, then concentrated under reduced pressure at 37° and freeze-dried after dilution with water. After gel filtration on Sephadex G 10 in acetic acid/water 1:1 and subsequent purification by preparative HPLC on a LiChrosorb RP8 column with an isopropanol gradient in 0.3% TFA/water, cyclo(D-Val-L-Phe-D-Asp-Gly-D-Arg) is obtained RT 17.9; M⁺ 575.

The following are obtained analogously:

from cyclo-(D-Val-D-Phe-D-Asp(OBut)-Gly-D-Arg (Mtr)): cyclo-(D-Val-D-Phe-D-Asp-Gly-D-Arg), RT 18.5; M⁺ 575;

from cyclo-(D-Val-D-Phe-L-Asp(OBut)-Gly-D-Arg (Mtr)): cyclo-(D-Val-D-Phe-L-Asp-Gly-D-Arg), RT 19.3; M⁺ 575;

from cyclo-(D-Val-D-Phe-D-Asp(OBut)-L-Ala-D-Arg (Mtr)): cyclo-(D-Val-D-Phe-D-Asp-L-Ala-D-Arg), RT 20.3; M⁺ 589;

from cyclo-(D-Val-D-Phe-D-Asp(OMe)-Gly-L-Arg (Mtr)): cyclo-(D-Val-D-Phe-D-Asp(OMe)-Giy-L-Arg), RT 21.4; M⁺589;

from cyclo-(D-Val-D-Phe-L-Asp(OBut)-Gly-L-Arg (Mtr)): cyclo-(D-Val-D-Phe-L-Asp-Gly-L-Arg);

from cyclo-(L-Val-D-Phe-D-Asp(OBut)-Gly-L-Arg (Mtr)): cyclo-(L-Val-D-Phe-D-Asp-Gly-L-Arg);

from cyclo-(D-Val-L-Phe-D-Asp(OBut)-Gly-L-Arg (Mtr)): cyclo-(D-Val-L-Phe-D-Asp-Gly-L-Arg);

from cyclo-(L-Val-D-Phe-L-Asp(OBut)-Gly-D-Arg (Mtr)): cyclo-(L-Val-D-Phe-L-Asp-Gly-D-Arg);

from cyclo-(D-Val-L-Phe-L-Asp(OBut)-Gly-D-Arg (Mtr)): cyclo-(D-Val-L-Phe-L-Asp-Gly-D-Arg);

from cyclo-(L-Val-L-Phe-D-Asp(OBut)-Gly-D-Arg (Mtr)): cyclo-(L-Val-L-Phe-D-Asp-Gly-D-Arg);

from cyclo-(L-Val-D-Phe-L-Asp(OBut)-D-Ala-L-Arg (Mtr)): cyclo-(L-Val-D-Phe-L-Asp-D-Ala-L-Arg);

from cyclo-(D-Val-L-Phe-L-Asp(OBut)-D-Ala-L-Arg (Mtr)): cyclo-(D-Val-L-Phe-L-Asp-D-Ala-L-Arg);

from cyclo-(L-Val-L-Phe-D-Asp(OBut)-D-Ala-L-Arg (Mtr)): cyclo-(L-Val-L-Phe-D-Asp-D-Ala-L-Arg);

from cyclo-(L-Val-L-Phe-L-Asp(OBut)-D-Ala-D-Arg (Mtr)): cyclo-(L-Val-L-Phe-L-Asp-D-Ala-D-Arg).

Example 2

A solution of 80 mg of H-L-Arg-D-Val-D-Phe-D-Asp (OMe)-Gly-ONa [obtainable by elimination of the FMOC group from FMOC-L-Arg-D-Val-D-Phe-D-Asp(OMe)-Gly-O-Wang (where O-Wang is the radical of a -4-oxymethylphenoxy-methyl polystyrene used in the Merrifield synthesis, which is crosslinked to 1% with p-divinylbenzene) using morpholine and elimination of the pentapeptide from the polymer using TFA/dichloromethane 1:1] in 8 ml of DMF is diluted with 72 ml of dichloromethane and treated with 34 mg of finely powdered NaHCO₃. After cooling in dry ice/acetone, 34 μl of diphenylphosphoryl azide are added. After standing at 20° for 16 hours, the dichloromethane is stripped off at 37°. The residual solution is gel-filtered (Sephadex G10 column in isopropanol/water 8:2) and then chromatographed in water on a polymer column (Mitsubishi MCI CHP-20P) in an isopropanol gradient. Cyclo-(D-Val-D-Phe-D -Asp(OMe)-Gly-L-Arg), RT 21.4; M⁺ 589, is obtained.

The examples below relate to pharmaceutical preparations.

Example A

Injection vials

A solution of 100 g of a cyclopeptide of the formula I and 5 g of disodium hydrogenphosphate in 3 l of doubly distilled water is adjusted to pH 6.5 with 2N hydrochloric acid, sterile filtered, filled into injection vials and lyophilized under sterile conditions, and the vials are closed in a sterile manner. Each injection vial contains 5 mg of active compound.

Example B

Suppositories

A mixture of 20 g of active compound of the formula I is fused with 100 g of soya lecithin and 1400 g of cocoa butter, and the mixture is poured into molds and allowed to cool. Each suppository contains 20 mg of active compound.

Example C

Solution

A solution of 1 g of active compound of the formula I, 9.38 g of NaH₂PO₄.2H₂O, 28.48 g of Na₂HPO₄.12H₂O and 0.1 g of benzalkonium chloride is prepared in 940 ml of doubly distilled water. The solution is adjusted to pH 6.8, made up to 1 l and sterilized by irradiation. This solution can be used in the form of eye drops.

Example D

Ointment 500 mg of active compound of the formula I are mixed with 99.5 g of petroleum jelly under aseptic conditions.

Example E

Tablets

A mixture of 100 g of a cyclopeptide of the formula I, 1 kg of lactose, 600 g of microcrystalline cellulose, 600 g of maize starch, 100 g of polyvinylpyrrolidone, 80 g of talc and 10 g of magnesium stearate is pressed to give tablets in a customary manner, such that each tablet contains 10 mg of active compound.

Example F

Coated tablets

Tablets are pressed as stated in Example E and then coated in a customary manner with a coating of sucrose, maize starch, talc, tragacanth and colorant.

Example G

Capsules

Hard gelatin capsules are filled with an active compound of the formula I in the customary manner, so that each capsule contains 5 mg of active compound.

Example H

Inhalation spray 14 g of active compound of the formula I are dissolved in 10 l of isotonic NaCl solution and the solution is filled into commercially available spray containers having a pump mechanism. The solution can be sprayed into the mouth or nose. One spray burst (about 0.1 ml) corresponds to a dose of about 0.14 mg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclopeptide of formula I cyclo-(a-b-c-d-Arg)                I wherein
a and b are each independently of one another Ala, Asn, Asp, Arg, Cys, Gln, Glu, Gly, His, Ile, Leu, Lys, Met, Phe, Pro, Ser, Thr, Trp, Tyr or Val;
c is Asp or Asp(O—$C_{1-4}$-alkyl); and
d is Gly or Ala;
wherein at least two of the amino acid radicals a,b,c, and d are present in the D-form; or
a salt thereof.

2. A compound according to claim 1, wherein said compound is cyclo-(D-Val-L-Phe-D-Asp-Gly-D-Arg).

3. A compound according to claim 1, wherein said compound is cyclo-(D-Val-D-Phe-D-Asp-Gly-L-Arg).

4. A compound according to claim 1, wherein said compound is cyclo-(D-Val-D-Phe-L-Asp-Gly-D-Arg).

5. A compound according to claim 1, wherein said compound is cyclo-(D-Val-D-Phe-D-Asp-L-Ala-D-Arg).

6. A compound according to claim 1, wherein said compound is cyclo-(D-Val-D-Phe-D-Asp(OMe)-Gly-L-Arg).

7. A compound according to claim 1, wherein c is Asp (O—$C_{1-4}$-alkyl) and alkyl is methyl, ethyl, isopropyl or tert.-butyl.

8. A compound according to claim 1, wherein a is Val.

9. A compound according to claim 8, wherein a is D-Val.

10. A compound according to claim 1, wherein a is Phe.

11. A compound according to claim 10, wherein b is D-Phe.

12. A compound according to claim 1, wherein c is Asp.

13. A compound according to claim 12, wherein c is D-Asp.

14. A compound according to claim 1, wherein c is Gly.

15. A compound according to claim 1, wherein a is D-Val, b is Phe, c is Asp or Asp(OMe) and d is Gly or Ala.

16. A compound according to claim 1, wherein said compound is:

cyclo-(D-Val-D-Phe-L-Asp-Gly-L-Arg);
cyclo-(L-Val-D-Phe-D-Asp-Gly-L-Arg);
cyclo-(D-Val-L-Phe-D-Asp-Gly-L-Arg);
cyclo-(L-Val-D-Phe-L-Asp-Gly-D-Arg);
cyclo-(D-Val-L-Phe-L-Asp-Gly-D-Arg);
cyclo-(L-Val-L-Phe-D-Asp-Gly-D-Arg);
cyclo-(L-Val-D-Phe-L-Asp-D-Ala-L-Arg);
cyclo-(D-Val-L-Phe-L-Asp-D-Ala-L-Arg);
cyclo-(L-Val-L-Phe-D-Asp-D-Ala-L-Arg); or
cyclo-(L-Val-L-Phe-L-Asp-D-Ala-D-Arg).

17. A pharmaceutical composition comprising an effective amount of a compound according to claim 1, and a pharmaceutically acceptable carrier.

18. A composition according to claim 17, wherein said composition contains 0.5–500 mg of said compound.

19. A composition according to claim 17, wherein said composition contains 0.5–100 mg of said compound.

20. A method for the treatment of thrombosis, cardiac infarct, arteriosclerosis, angina pectoris, angiogenesis or restenosis after angioplasty, comprising administering to a patient an effective amount of a compound according to claim 1.

21. A method according to claim 20, wherein said compound is administered in an amount of 0.01–2 mg/kg of body weight.

22. A method according to claim 21, said compound is administered in an amount of 0.01–2 mg/kg of body weight.

23. A method of binding to a $\beta_3$-integrin receptor, comprising contacting a compound according to claim 1 with a sample containing $\beta_3$-integrin receptors, under conditions in which said compound binds to said integrin receptor.

* * * * *